United States Patent [19]

Razdan et al.

[11] 4,260,617
[45] Apr. 7, 1981

[54] 17-CYCLOPROPYLMETHYL-14-HYDROXY-3-METHOXYMORPHINAN-6-ONE AND METHOD OF TREATING PAIN WITH IT

[75] Inventors: Raj K. Razdan, Belmont; Anil C. Ghosh, Lexington, both of Mass.

[73] Assignee: SISA, Incorporated, Cambridge, Mass.

[21] Appl. No.: 104,587

[22] Filed: Dec. 17, 1979

[51] Int. Cl.³ .................. A61K 31/485; C07D 221/28
[52] U.S. Cl. ..................................... 424/260; 546/74
[58] Field of Search .......................... 546/74; 424/260

[56] References Cited

U.S. PATENT DOCUMENTS

| | | | |
|---|---|---|---|
| 3,166,559 | 1/1965 | Sawa et al. | 546/74 |
| 3,201,403 | 8/1965 | Sawa et al. | 546/74 |
| 3,738,989 | 6/1973 | Sawa et al. | 546/74 |

OTHER PUBLICATIONS

Kotick, et al., J. Med. Chem. 23, 166–174 (1980).
Polazzi, et al., J. Med. Chem. 23, 174–179 (1980).

*Primary Examiner*—Donald G. Daus
*Assistant Examiner*—Diana G. Rivers
*Attorney, Agent, or Firm*—Jerome L. Jeffers

[57] ABSTRACT

Disclosed is 17-cyclopropylmethyl-14-hydroxy-3-methoxymorphinan-6-one. This compound is a mixed agonist (analgesic)/narcotic antagonist and therefore useful for the treatment of moderate to severe pain without the liability of inducing physical dependence.

6 Claims, No Drawings

17-CYCLOPROPYLMETHYL-14-HYDROXY-3-METHOXYMORPHINAN-6-ONE AND METHOD OF TREATING PAIN WITH IT

BACKGROUND OF THE INVENTION

1. Field of the Invention

Morphine is a well known narcotic/analgesic having the structural formula:

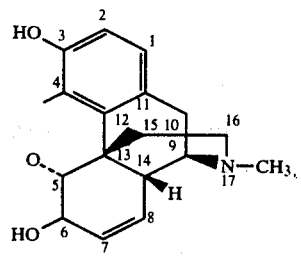

The compound of this invention is structurally related to morphine and is named according to the morphinan system of nomenclature using the morphinan nucleus which is shown below:

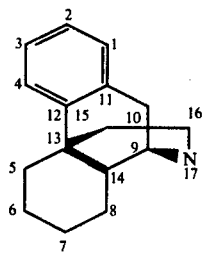

The numbering and stereochemical placement of atoms in the morphinan system is the same as that depicted for morphine. A dashed line is used to represent a covalent bond projecting below the plane of a reference atom while a wedged or heavily accented line signifies a covalent bond above such plane. The compound of this invention has the same stereochemical placement of atoms as depicted for morphine.

Morphine and its structrually related relatives are used primarily as analgesics. While extremely effective for the relief of moderate to severe pain these compounds are narcotic and most possess dependence-inducing ability and produce other side effects such as emesis, constipation, sweating, respiratory depression and myosis which make less than ideal analgesics. It is impossible to predict, based on structure alone, whether a particular morphine-like compound will act as an analgesic (agonist), a narcotic antagonist or possess a combination of these properties since very minute structural modifications in the molecule result in significant changes in pharmacological activity. A compound with the appropriate profile of analgesic (agonist) and narcotic antagonist actions has potential for treatment of moderate to severe pain without the liability of drug dependence or drug abuse.

PRIOR ART

Morphinans which are hydroxy substituted in the 14-position are known. Thus, I. J. Pachter reports in *Narcotic Antagonists, Advances in Biochemical Psychopharmacology*, Vol. 8, Raven Press, New York 1973, p. 57, the preparation of compounds having the structure:

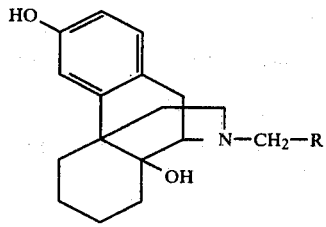

where R is cyclopropyl (A) or cyclobutyl (B). The compound in which R is cyclopropyl is reported to be essentially a narcotic antagonist while that compound in which R is cyclobutyl is reported to possess both analgesic and narcotic antagonist activity. This article also reports the preparation by the Shionogi Company in Japan of a compound having the formula:

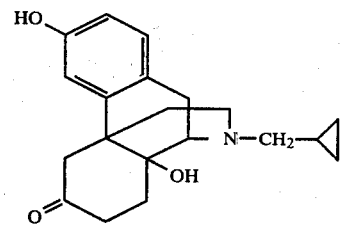

It is stated that this compound is very long acting and more potent than A (above), cyclazocine or naloxone. Naloxone is a potent narcotic antagonist whereas cyclazocine has mixed analgesic/narcotic antagonist activity. The pharmacology of this compound, in terms of its analgesic and narcotic antagonist activity, is not disclosed in the Pachter article.

SUMMARY OF THE INVENTION

The present invention is a novel analgesic (agonist)/narcotic antagonist, 17-cyclopropylmethyl-14-hydroxy-3-methoxymorphinan-6-one, characterized by the structural formula:

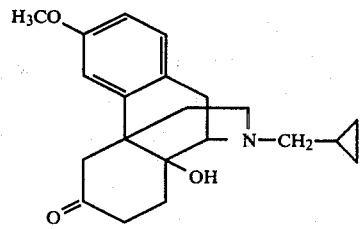

and pharmaceutically acceptable, nontoxic acid addition salts thereof.

DETAILED DESCRIPTION

The preparation of the compound claimed herein, its prior art 3-hydroxy homologue and the pharmacology of these compounds are described in the following examples:

EXAMPLE I

Preparation of 17-cyclopropylmethyl-14-hydroxy-3-methoxymorphinan-6-one hydrochloride (179-A-19)

A. Preparation of 17-cyano-14-hydroxy-3-methoxy-morphinan-6-one II

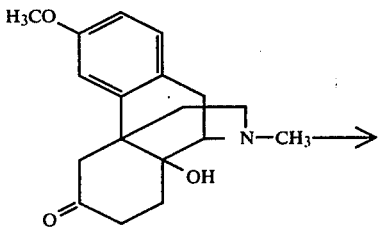

I

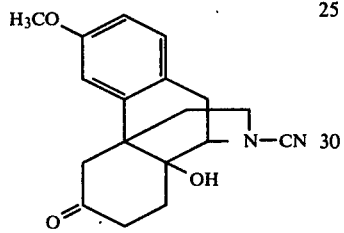

II

Compound I, which can be prepared by the method described by Sawa et al. in Tetrahedron, Vol. 24, Pp 6185–6196, (1.2 g), CNBr (3.5 g), K$_2$CO$_3$ (5 g) and CH$_2$Cl$_2$ (70 ml) were refluxed with stirring under a nitrogen atmosphere for 18 hours to give product which was filtered and the filtrate concentrated in vacuo to give Crude II (yield 0.957 g) the structure of which was confirmed by thin layer chromatography (tlc) and nuclear magnetic resonance (nmr).

B. Preparation of 14-hydroxy-3-methoxymorphinan-6-one hydrochloride III

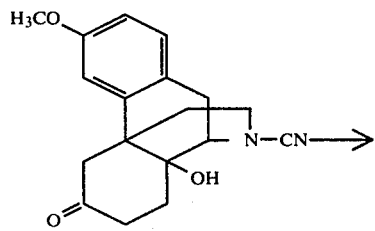

II

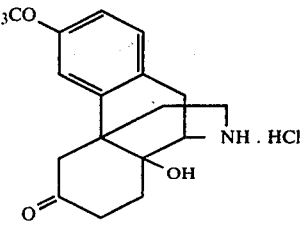

III

A mixture of Compound II (0.950 g) and 2 N HCl (120 ml) was refluxed under a nitrogen atmosphere with stirring for 6 hours to give a product which was concentrated in vacuo to give Crude III as a solid (yield 1.01 g) the structure of which was confirmed by tlc and nmr. C. Preparation of 17-cyclopropylmethyl-14-hydroxy-3-methoxymorphinan-6-one hydrochloride IV

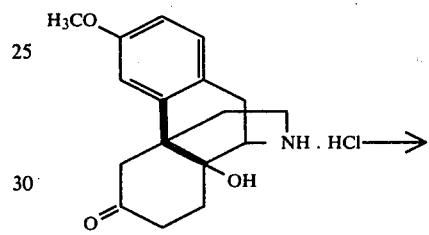

III

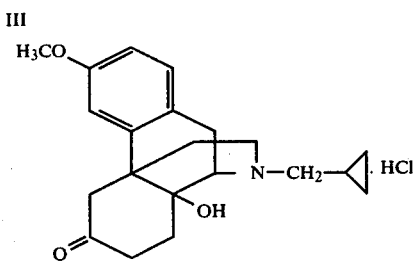

IV

A mixture of Compound III (1 g),

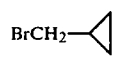

(2.3 g), NaHCO$_3$ (4 g) and dimethylformamide (DMF) (60 ml) was heated with stirring under a nitrogen atmosphere for 19 hours (oil bath temperature 110°–115° C.). The reaction mixture was filtered and the solid washed with DMF whereupon most of the DMF was removed by distillation under reduced pressure (high vacuum; temperature 50°–60° C.). The residue was treated with water (30 ml) and extracted with CHCl$_3$ (3×100 ml) and ethyl acetate (3×100 ml) after saturating the aqueous layer with NaCl. The organic solutions were separately washed, combined and dried over MgSO$_4$. Filtration and concentration under vacuum gave Crude IV (1.05 g) which was chromatographed over silica gel using CHCl$_3$ and graded MeOH-CHCl$_3$ as eluant. The structure of this product was confirmed by tlc and nmr.

A portion of Compound IV was converted to its hydrochloride salt by combining it with concentrated HCl in 10 ml of ethanol and evaporating the solvent. Toluene was added and the solution concentrated to dryness under vacuum. The residue was dissolved in a small amount of MeOH whereupon ethyl acetate was added and the solution concentrated at which point the solid was collected. This material whose structure was confirmed by mass spectral and elemental analysis was designated 179-A-19 and tested as described in Example III, infra. The other portion was left in the form of its free base and used in the experiment described in Example II.

EXAMPLE II

Preparation of 17-cyclopropylmethyl-3,14-dihydroxymorphinan-6-one hydrochloride (V)

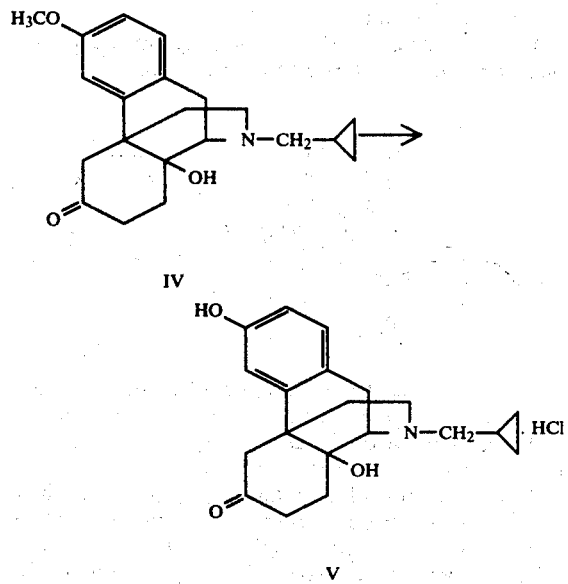

A solution of IV (0.300 g) in CHCl$_3$ (50 ml) was added to a solution of BBr$_3$ (2.5 g) in CHCl$_3$ (50 ml) and the mixture stirred at room temperature for 40 minutes. At this point the mixture was treated with NH$_4$OH (50 ml) and ice (10 g) and the mixture stirred at 0°–5° C. for 1 hour. The CHCl$_3$ layer was separated and the aqueous layer saturated with NaCl and re-extracted with CHCl$_3$ (3×50 ml) followed by ethyl acetate. After washing, the combined organic solutions were dried (MgSO$_4$) filtered and concentrated to give 272 mg of Crude V (free base). The crude product was chromatographed over silica gel using CHCl$_3$ and graded MeOH-CHCl$_3$ as eluant to give 153 mg of purified product whose structure was confirmed by tlc and nmr.

At this point, the product was taken up in ethanol (10 ml) and 3 ml of concentrated HCl was added whereupon the solvent was removed via a rotary evaporator. Toluene was added and the solvent removed again. Additional toluene and ethanol were added and the solution evaporated to a dry solid which was taken up in methanol, filtered and the filtrate concentrated to some extent. Ethyl acetate was added followed by drops of diethyl ether and 102 mg of solid product was obtained after filtration and drying to provide the title compound V which was assigned the code number 179-A-20. The structure of this material, i.e., the hydrochloric acid addition salt of the compound prepared as described in the preceding paragraph, was confirmed by mass spectral and elemental analysis.

EXAMPLE III

PHARMACOLOGICAL EVALUATION

The compounds whose preparation is disclosed in the foregoing examples were screened to determine the following biological activities:
(A) Analgesic effects upon mice (acetic acid writhing test).
(B) Narcotic antagonist activity in rats (modified rat tail flick test).

TEST A. ACETIC ACID MOUSE WRITHING TEST

The analgesic effects of test compounds were determined in mice by use of the acetic acid writhing test described by B. J. R. Whittle, Brit. J. Pharmacol., 22: 296 (1964). In this test at least three groups of five male CD-1 mice each were given subcutaneous doses of the test drug dissolved in either distilled water or distilled water acidified with HCl depending on the solubility of the compound. In all cases, 0.4 milliliter of a 0.75% V/V acetic acid in distilled water solution was administered intraperitoneally 15 minutes post drug. The number of writhes in a 20 minute interval were determined and compared with the number of writhes in control groups which had received only acetic acid.

Percent inhibition of writhing was calculated as:

$$\% \text{ inhibition} = \frac{\text{No control writhes} - \text{No treated writhes}}{\text{No. control writhes}} \times 100$$

The ED$_{50}$ dose, i.e., the dose required to reduce the number of writhes by 50%, was determined graphically from a plot of % inhibition as a probit versus log dose. Confidence limits of 95% were calculated on the basis of those results falling in the range 16–84% inhibition. See Litchfield, J. T. and Wilcoxon, F., J. Pharmacol. Exp. Ther., 96, 99-113, (1949).

TEST B. EVALUATION OF NARCOTIC ANTAGONIST ACTIVITY

The narcotic antagonist effects of test compounds were determined by a modification of the rat tail flick procedure of Harris and Pierson (J. Pharmacol. Exp. Ther. 143: 141 [1964]).

Male albino Wistar rats (100–120 g) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp, is used to adjust the intensity of the light fallng on the tail of the rat such that the rat's control reaction time is from two to four seconds. Animals with a control reaction time outside this range are rejected. The rheostat adjustment is made only if a significant proportion (more than 1 out of every 10 rats) of the reaction times are outside the range of 1.8 to 5.8 seconds. Groups of five rats were used each time, and two control times were determined at least 30 minutes apart. The test drug was given intraperitoneally and this was followed ten minutes later by an ED$_{80}$ dose of morphine subcutaneously. The animals were retested at 20 minutes after the morphine injection. Control animals were given morphine only. A ten second cut off time is employed; if the rat does not flick its tail in 10 seconds it is removed from the heat source.

The data were calculated as follows:

$$\% \text{ Effect } (E) = \frac{MRT^*(\text{Treated}) - MRT(\text{Control})}{10 - MRT(\text{Control})} \times 100$$

$$\% \text{ Antagonism} = \frac{E(\text{morphine controls}) - E(\text{drug treated})}{E(\text{morphine control})} \times 100$$

*MRT is defined as mean reaction time.

The data were plotted on log-probit paper and $AD_{50}$ values, i.e., the dose required to inhibit the morphine effect by 50% within 95% confidence limits, were determined by the method of Litchfield and Wilcoxon.

The results of these tests, which where conducted on the compounds prepared in Examples I and II, are set out in Table I.

TABLE I

| Compounds | Ex. | $ED_{50}$ Mg/Kg | $AD_{50}$ Mg/Kg | $ED_{50}/AD_{50}$ |
|---|---|---|---|---|
| 179-A-19 | I | 0.3 | 0.5 | 0.6 |
| 179-A-20 | II | 2.2 | 0.082 | 26.83 |

From Table I, it can be determined that the novel compound claimed herein, 179-A-19, is more potent than the closest prior art compound, 179-A-20 as an analgesic, by a factor of greater than 7. Conversely, the prior art compound is more potent in terms of narcotic antagonist activity by a factor of about 6. The clinical superiority of 179-A-19 Vis-a-vis 179-A-20 can be determined from the ratio of $ED_{50}$ to $AD_{50}$. This is the case because it has been determined from a survey of the open literature concerning clinical experience with compounds of this type that those with a high ratio tend to be much more likely to cause adverse CNS side effects than are those compounds with a low ratio. Thus, 179-A-19 which is a very potent analgesic and also a potent narcotic antagonist, would be suitable for use as a strong/non-addictive analgesic in humans because of its low tendency towards causing adverse CNS side effects. Conversely, 179-A-20 with its high ratio of $ED_{50}$ to $AD_{50}$ would not be expected to be clinically useful because of its high tendency towards causing adverse CNS side effects.

The compound of the present invention forms pharmacologically acceptable addition salts with organic and inorganic acids. Typical acid addition salts are the tartrate, hydrobromide, hydrochloride and maleate. The hydrochloride is preferred. As previously stated, it is suitable for relieving moderate to severe pain in an individual for whom such therapy is indicated without the liability of causing drug dependence or adverse CNS side effects.

The term "individual" means a human being or an experimental animal that is a model for a human being. The dose to be administered to achieve the desired result, i.e., the effective dose, may vary from individual to individual but is readily determined by one skilled in the art without undue experimentation.

The compound of the present invention may be administered by known, conventional methods of therapeutic administration such as intravenous, parenteral, buccal, rectal or oral. Dose forms for the administration of this compound can be prepared by methods recognized in the pharmaceutical sciences.

What is claimed is:

1. 17-cyclopropylmethyl-14-hydroxy-3-methoxymorphinan-6-one characterized by the formula:

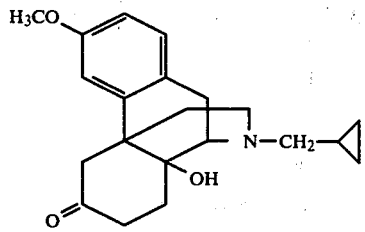

2. The compound of claim 1 in the form of its pharmacologically acceptable, nontoxic acid addition salt.

3. The compound of claim 2 in the form of its hydrochloric acid addition salt.

4. A therapeutic method for treating pain in an individual for whom such therapy is indicated, which method comprises administering to the individual an effective analgesic amount of 17-cyclopropylmethyl-14-hydroxy-3-methoxymorphinan-6-one.

5. The method of claim 4 wherein the compound is administered in the form of its pharmacologically acceptable, nontoxic acid addition salt.

6. The method of claim 5 wherein the compound is administered in the form of its hydrochloric acid addition salt.